United States Patent
Choi et al.

(10) Patent No.: US 8,262,648 B2
(45) Date of Patent: Sep. 11, 2012

(54) CONTROL METHOD AND STRUCTURE OF LASER BEAM IRRADIATION BY USING A CONTACT SENSOR

(75) Inventors: Hak Ki Choi, Seoul (KR); Tae Ho Ha, Goyang (KR); Hae Lyung Hwang, Gimpo (KR); Sung Huan Gong, Seoul (KR)

(73) Assignee: Lutronics Corporation (KR)

( * ) Notice: Subject to any disclaimer, the term of this patent is extended or adjusted under 35 U.S.C. 154(b) by 646 days.

(21) Appl. No.: 12/294,387

(22) PCT Filed: Apr. 26, 2006

(86) PCT No.: PCT/KR2006/001579
§ 371 (c)(1),
(2), (4) Date: Oct. 5, 2009

(87) PCT Pub. No.: WO2007/111397
PCT Pub. Date: Oct. 4, 2007

(65) Prior Publication Data
US 2010/0042083 A1 Feb. 18, 2010

(30) Foreign Application Priority Data

Mar. 27, 2006 (KR) .......... 10-2006-0027384

(51) Int. Cl.
*A61B 18/18* (2006.01)
(52) U.S. Cl. .......... 606/12; 606/11; 606/10; 606/9; 607/89
(58) Field of Classification Search .......... 606/12, 606/11, 10, 9; 607/89
See application file for complete search history.

(56) References Cited

U.S. PATENT DOCUMENTS

| | | | |
|---|---|---|---|
| 5,112,328 A | 5/1992 | Taboada et al. | |
| 5,312,396 A | 5/1994 | Feld et al. | |
| 5,408,186 A * | 4/1995 | Bakhoum | 324/509 |
| 5,662,590 A | 9/1997 | de la Torre et al. | |
| 5,707,401 A | 1/1998 | Talmore | |
| 5,766,214 A | 6/1998 | Mehl, Sr. et al. | |
| 5,843,071 A | 12/1998 | Bath | |
| 5,873,875 A | 2/1999 | Altshuler | |
| 5,885,211 A | 3/1999 | Eppstein et al. | |
| 5,919,186 A | 7/1999 | Bath | |
| 5,984,916 A | 11/1999 | Lai | |

(Continued)

FOREIGN PATENT DOCUMENTS

JP 6190071 A 7/1994

(Continued)

*Primary Examiner* — Kinam Park
(74) *Attorney, Agent, or Firm* — Pepper Hamilton LLP

(57) ABSTRACT

The present invention relates to a laser beam control structure and method. A laser beam control structure of the present invention comprises a handpiece for irradiating laser beams output from a laser beam output device, on a predetermined part; at least one electrode unit positioned at a human body contact portion of the handpiece and receiving hum noise generated from a human body; and a control unit electrically connected to the electrode unit so as to measure the hum noise applied from the electrode unit and to cause the laser beams to be irradiated according to the measured hum noise. According to the present invention, there are advantages in that various types of hum noise generated from a human body are measured without applying an electric current to the human body, and a laser beam is irradiated according to the measured hum noise.

4 Claims, 2 Drawing Sheets

U.S. PATENT DOCUMENTS

| | | | |
|---|---|---|---|
| 6,063,108 | A | 5/2000 | Salansky et al. |
| 6,096,031 | A | 8/2000 | Mitchell et al. |
| 6,149,671 | A | 11/2000 | Nordquist et al. |
| 6,200,309 | B1 | 3/2001 | Rice et al. |
| 6,242,477 | B1 | 6/2001 | Okamoto et al. |
| 6,267,755 | B1 | 7/2001 | Clementi et al. |
| 6,277,111 | B1 | 8/2001 | Clement et al. |
| 6,379,376 | B1 | 4/2002 | Lubart |
| 6,387,089 | B1 | 5/2002 | Kreindel et al. |
| 6,494,900 | B1 | 12/2002 | Salansky et al. |
| 6,524,329 | B1 | 2/2003 | Benedict |
| 6,530,915 | B1 | 3/2003 | Eppstein et al. |
| 6,595,986 | B2 | 7/2003 | Almeida |
| 6,605,080 | B1 | 8/2003 | Altshuler et al. |
| 6,607,523 | B1 | 8/2003 | Asah et al. |
| 6,613,040 | B2 | 9/2003 | Tankovich et al. |
| 6,676,655 | B2 | 1/2004 | McDaniel |
| 6,685,730 | B2 | 2/2004 | West et al. |
| 6,770,069 | B1 | 8/2004 | Hobart et al. |
| 6,786,899 | B1 | 9/2004 | Lai |
| 6,936,044 | B2 | 8/2005 | McDaniel |
| 6,962,584 | B1 | 11/2005 | Stone et al. |
| 6,997,923 | B2 | 2/2006 | Anderson et al. |
| 7,041,093 | B2 | 5/2006 | Toftkjaer |
| 7,097,656 | B1 | 8/2006 | Akopov et al. |
| 7,101,384 | B2 | 9/2006 | Benedict |
| 7,108,692 | B2 | 9/2006 | Frenz et al. |
| 7,160,289 | B2 | 1/2007 | Cohen |
| 7,282,060 | B2 | 10/2007 | DeBenedictis et al. |
| 7,283,576 | B2 | 10/2007 | Krupke |
| 7,306,620 | B2 | 12/2007 | Cumbie |
| 7,309,335 | B2 | 12/2007 | Altshuler et al. |
| 7,329,252 | B1 | 2/2008 | Yamazaki et al. |
| 7,331,953 | B2 | 2/2008 | Manstein et al. |
| 7,351,241 | B2 | 4/2008 | Bendett et al. |
| 7,351,252 | B2 | 4/2008 | Altshuler et al. |
| 7,353,829 | B1 | 4/2008 | Wachter et al. |
| 7,354,448 | B2 | 4/2008 | Altshuler et al. |
| 2001/0001118 | A1 | 5/2001 | Asah et al. |
| 2001/0050083 | A1 | 12/2001 | Marchitto et al. |
| 2002/0019624 | A1 | 2/2002 | Clement et al. |
| 2002/0103482 | A1 | 8/2002 | Scholler et al. |
| 2002/0161357 | A1 | 10/2002 | Anderson et al. |
| 2003/0004556 | A1 | 1/2003 | McDaniel |
| 2003/0023283 | A1 | 1/2003 | McDaniel |
| 2003/0216719 | A1 | 11/2003 | Debenedictis et al. |
| 2004/0093042 | A1 | 5/2004 | Altshuler et al. |
| 2004/0162596 | A1 | 8/2004 | Altshuler et al. |
| 2004/0167500 | A1* | 8/2004 | Weckwerth et al. ............... 606/9 |
| 2004/0199152 | A1 | 10/2004 | Key |
| 2004/0199223 | A1 | 10/2004 | Andersen et al. |
| 2004/0225339 | A1 | 11/2004 | Yaroslavsky et al. |
| 2004/0230258 | A1 | 11/2004 | Altshuler et al. |
| 2004/0243111 | A1 | 12/2004 | Bendett et al. |
| 2004/0243114 | A1* | 12/2004 | Yamazaki et al. ................ 606/9 |
| 2005/0004632 | A1 | 1/2005 | Benedict |
| 2005/0015123 | A1 | 1/2005 | Paithankar |
| 2005/0049582 | A1 | 3/2005 | DeBenedictis et al. |
| 2005/0049658 | A1 | 3/2005 | Connors et al. |
| 2005/0119642 | A1 | 6/2005 | Grecu et al. |
| 2005/0154380 | A1 | 7/2005 | DeBenedictis et al. |
| 2005/0154381 | A1 | 7/2005 | Altshuler et al. |
| 2005/0203495 | A1 | 9/2005 | Malak |
| 2005/0215987 | A1 | 9/2005 | Slatkine |
| 2005/0222555 | A1 | 10/2005 | Manstein et al. |
| 2005/0251231 | A1 | 11/2005 | Goldberg |
| 2006/0020309 | A1 | 1/2006 | Altshuler et al. |
| 2006/0079947 | A1 | 4/2006 | Tankovich et al. |
| 2006/0095095 | A1 | 5/2006 | Cao |
| 2006/0095096 | A1 | 5/2006 | DeBenedictis et al. |
| 2006/0189967 | A1 | 8/2006 | Masotti et al. |
| 2006/0217787 | A1 | 9/2006 | Olson et al. |
| 2006/0253178 | A1 | 11/2006 | Masotti |
| 2006/0259102 | A1 | 11/2006 | Slatkine |
| 2007/0005120 | A1 | 1/2007 | Villacampa et al. |
| 2007/0027441 | A1 | 2/2007 | Almeida |
| 2007/0032847 | A1 | 2/2007 | Weckwerth et al. |
| 2007/0073367 | A1 | 3/2007 | Jones et al. |
| 2007/0078500 | A1 | 4/2007 | Ryan et al. |
| 2007/0123844 | A1 | 5/2007 | Henry |
| 2007/0198068 | A1 | 8/2007 | Chan et al. |
| 2007/0219601 | A1 | 9/2007 | Neuberger |
| 2007/0260229 | A1 | 11/2007 | Navarro et al. |
| 2008/0015554 | A1 | 1/2008 | Cole et al. |
| 2008/0015556 | A1 | 1/2008 | Chan et al. |
| 2008/0015557 | A1 | 1/2008 | Chan et al. |
| 2008/0033516 | A1 | 2/2008 | Altshuler et al. |
| 2008/0045933 | A1 | 2/2008 | Perl |
| 2008/0058783 | A1 | 3/2008 | Altshuler et al. |
| 2008/0058784 | A1 | 3/2008 | Manstein et al. |
| 2008/0058904 | A1 | 3/2008 | Hillis et al. |
| 2008/0091179 | A1 | 4/2008 | Durkin et al. |
| 2008/0147052 | A1 | 6/2008 | Bendett et al. |
| 2008/0154344 | A1 | 6/2008 | Trusty et al. |
| 2008/0183250 | A1 | 7/2008 | Tanojo et al. |
| 2008/0208178 | A1 | 8/2008 | DeBenedictis et al. |
| 2008/0208179 | A1 | 8/2008 | Chan et al. |
| 2008/0215040 | A1 | 9/2008 | Paithankar et al. |
| 2008/0234786 | A1 | 9/2008 | Cumbie |
| 2008/0262577 | A1 | 10/2008 | Altshuler et al. |

FOREIGN PATENT DOCUMENTS

| | | |
|---|---|---|
| JP | 2003300684 | 10/2003 |
| JP | 2003310639 | 11/2003 |
| JP | 2005034609 A | 2/2005 |
| KR | 2005051095 A | 6/2005 |
| KR | 200408926 Y1 | 2/2006 |
| WO | WO 03/028807 A1 | 4/2003 |
| WO | WO 2004/037068 A2 | 5/2004 |

* cited by examiner

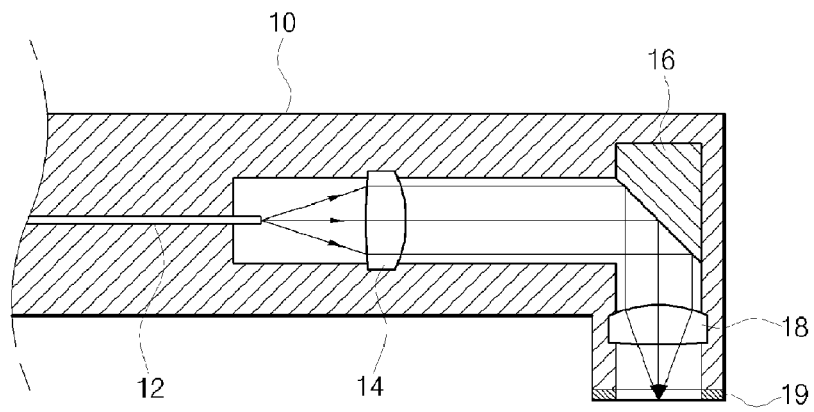
[Fig. 1]
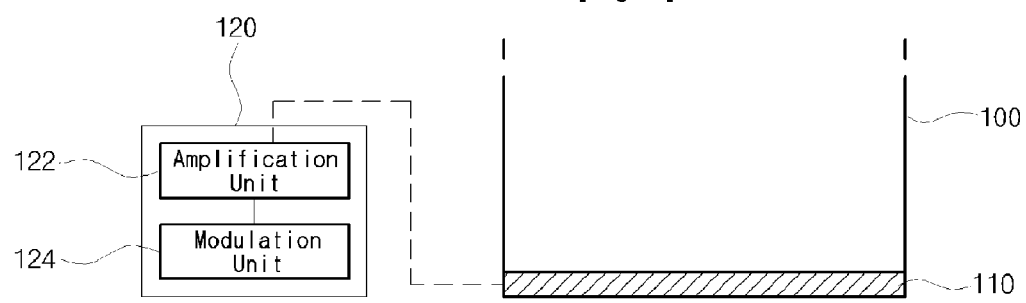
[Fig. 2]
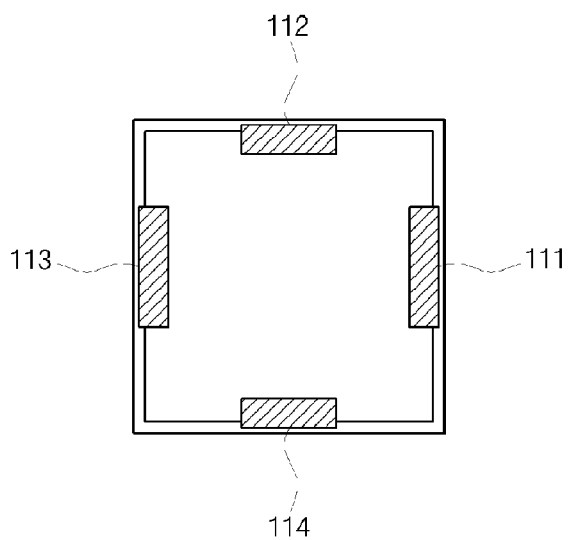
[Fig. 3]

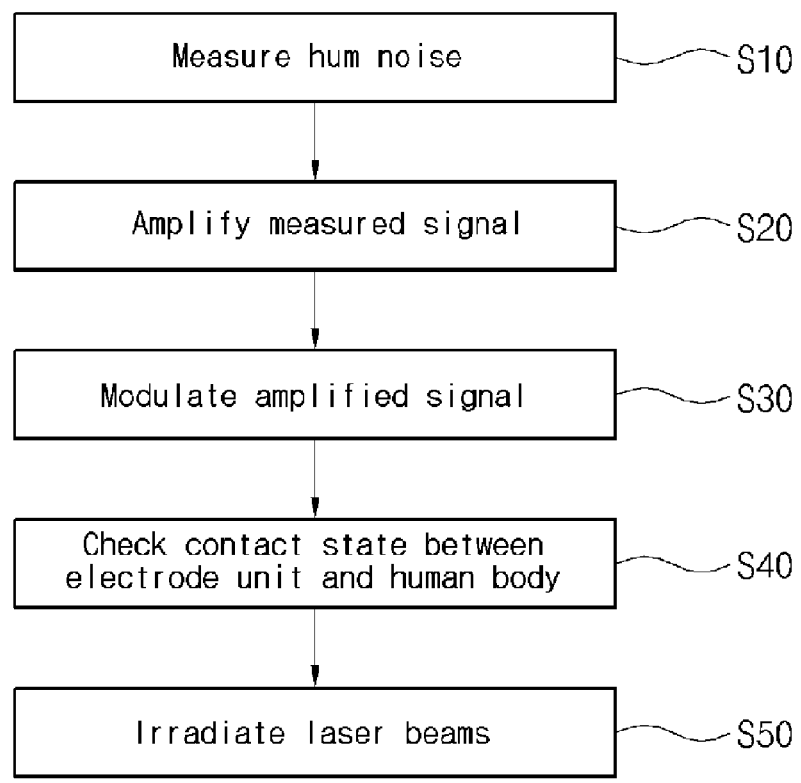

CONTROL METHOD AND STRUCTURE OF LASER BEAM IRRADIATION BY USING A CONTACT SENSOR

CROSS REFERENCE TO RELATED APPLICATIONS

This application is a U.S. national stage filing under 35 U.S.C. §371 of PCT Application PCT/KR2006/001579 filed Apr. 26, 2006, which claims priority to KR 10-2006-0027384 filed Mar. 27, 2006.

TECHNICAL FIELD

The present invention relates to a laser beam control structure and method, and more particularly, to a laser beam control structure and method, wherein various types of hum noise generated from a human body are measured without applying an electric current to the human body, and a laser beam is irradiated according to the measured hum noise.

BACKGROUND ART

Generally, in micro fractional ablation that has been recently developed as a clinical method for dermatological treatment, a micro laser beam is irradiated in various patterns on a certain area of the skin. At this time, a handpiece tip should be in contact with the skin so that the size of the laser beam can be maintained accurately. Various contact sensors have been used to determine whether the handpiece tip is in contact with the skin.

Referring to FIG. 1, a conventional laser beam handpiece comprises a laser fiber 12 made of sapphire to irradiate laser beams, which are output from a laser beam output device (not shown), in a handpiece body 10; a collimating lens 14 for converting the laser beams irradiated from the laser fiber 12 into collimated light; a reflector 16 for changing a beam path of the laser beams output through the collimated lens 14; and a focusing lens 18 for focusing the laser beams reflected by the reflector so that the laser beams can be irradiated on a position. One of contact sensors to be employed at this time is an electrically operated contact sensor in which at least two electrodes 19 electrically insulated to each other are mounted at certain portions on a handpiece tip (not shown) and a predetermined voltage is applied between the electrodes. When the electrodes are in contact with the skin, a certain electric current flows through the skin. The electric current is measured to check a state where the electrodes are in contact with the skin. Only when the handpiece tip is in contact with the skin, a laser can be oscillated and micro laser beams can be irradiated on the skin.

However, in the method of measuring an electric current flowing through a human body, the amplitude of an electric current flowing when two electrodes are in contact with the skin varies according to persons and skin resistance depends on parts to be treated or skin conditions. As a result, there is a problem in that it takes much time to differently deal with respective conditions.

DISCLOSURE OF INVENTION

Technical Problem

Accordingly, the present invention is conceived to solve the aforementioned problems. An object of the present invention is to provide a laser beam control structure and method, wherein various types of hum noise generated from a human body are measured without applying an electric current to the human body, and a laser beam is irradiated according to the measured hum noise.

Technical Solution

To achieve the object of the present invention, a laser beam control structure of the present invention comprises a handpiece for irradiating laser beams output from a laser beam output device, on a predetermined part; at least one electrode unit positioned at a human body contact portion of the handpiece and receiving hum noise generated from a human body; and a control unit electrically connected to the electrode unit so as to measure the hum noise applied from the electrode unit and to cause the laser beams to be irradiated according to the measured hum noise.

The control unit may comprise an amplification unit for amplifying the measured hum noise; and a modulation unit for converting the hum noise applied from the amplification unit into a digital signal.

A laser beam control method of the present invention comprises the steps of: 1) measuring hum noise generated from a human body; 2) checking a contact state between the electrode unit and a human body; and 3) checking, based on the measured hum noise, whether laser beams will be irradiated and irradiating the laser beams. Step 1) further comprises the steps of amplifying the measured hum noise; and converting the amplified hum noise into a digital signal.

Advantageous Effects

The present invention constructed as above has the following advantages.

According to the present invention, there are advantages in that various types of hum noise generated from a human body are measured without applying an electric current to the human body, and a laser beam is irradiated according to the measured hum noise.

Further, there is an advantage in that a handpiece can be in perpendicular contact with a human body to ensure more effective irradiation of laser beams.

BRIEF DESCRIPTION OF THE DRAWINGS

FIG. 1 is a sectional view showing the structure of a conventional handpiece.

FIG. 2 is a schematic view showing a laser beam control structure according to the present invention.

FIG. 3 is a schematic view showing the configuration of an electrode unit of the laser beam control structure according to the present invention.

FIG. 4 is a block diagram illustrating a laser beam control method according to the present invention.

BEST MODE FOR CARRYING OUT THE INVENTION

Hereinafter, a laser beam control structure of the present invention will be described in detail with reference to the accompanying drawings.

Referring to FIG. 2, the laser beam control structure comprises a handpiece 100 for irradiating laser beams output from a laser beam output device, on a predetermined part; at least one electrode unit 110 positioned at a human body contact portion of the handpiece 100 and receiving hum noise generated from a human body; and a control unit 120 electrically connected to the electrode unit 110 so as to measure the hum noise applied from the electrode unit 110 and to cause the laser beams to be irradiated according to the measured hum noise.

As shown in FIG. 3, the electrode unit 110 comprises four electrodes 111, 112, 113 and 114 arranged at a predetermined interval. The respective electrodes are constructed to come into contact with the human body and to receive the hum noise generated from the human body. Further, when all the four electrodes 111, 112, 113 and 114 are in contact with the human body, the handpiece 100 irradiates the laser beams, resulting in efficient skin treatment.

The control unit 120 comprises an amplification unit 122 for amplifying the measured hum noise; and a modulation unit 124 for converting the hum noise applied from the amplification unit 122 into a digital signal, and functions to apply a signal for causing the handpiece 100 to irradiate the laser beams in response to an electrode contact signal from the electrode unit 110. Here, any control circuit may be used for the control unit 120 so far as the control circuit can amplify and digitalize the hum noise applied from the electrodes.

Referring to FIG. 4, a laser beam control method comprises the steps of measuring hum noise generated from a human body (S10); checking a contact state between the electrode unit and a human body (S40); and checking, based on the measured hum noise, whether laser beams will be irradiated and irradiating the laser beams (S50). It is preferred that between the measuring step S10 and the human body contact state checking step S40, the laser beam control method further comprise the steps of amplifying the measured hum noise (S20), and converting the amplified hum noise into a digital signal (S30).

That is, when the electrode unit comes into contact with the human body in the measuring step, specific hum noise is generated from the human body. Accordingly, the electrode unit receives the hum noise in the measuring step, thereby preventing the occurrence of an error due to application of an electric current to the human body, and ensuring fast and rapid measurement regardless of various conditions of the human body. Further, the applied hum noise is amplified and digitalized so that a user can easily recognize the hum noise.

Further, when the electrode unit completely comes into contact with the human body, the control unit causes the laser beams to be irradiated, so that the human body can be treated in a state where the handpiece is always perpendicular to the human body, resulting in improved efficiency.

The present invention is not limited to the embodiments described above, and those skilled in the art can make various modifications and changes thereto. The modifications and changes fall within the spirit and scope of the present invention defined by the appended claims.

The invention claimed is:

1. A laser beam control structure, comprising:
    a handpiece for irradiating laser beams output from a laser beam output device, on a predetermined part;
    at least one electrode unit positioned at a human body contact adapted portion of the handpiece and receiving hum noise adapted to be generated from a human body; and
    a control unit electrically connected to the electrode unit so as to measure the hum noise applied from the electrode unit and to cause the laser beams to be irradiated according to the measured hum noise.

2. The laser beam control structure as claimed in claim 1, wherein the control unit comprises an amplification unit for amplifying the measured hum noise; and a modulation unit for converting the hum noise applied from the amplification unit into a digital signal.

3. A laser beam control method, comprising the steps of:
    1) measuring hum noise adapted to be generated from a human body; 2) checking a contact state adapted between the electrode unit and a human body; and
    3) checking, based on the measured hum noise, whether laser beams will be irradiated and irradiating the laser beams.

4. The laser beam control method as claimed in claim 3, wherein said step 1) further comprises the steps of:
    amplifying the measured hum noise; and
    converting the amplified hum noise into a digital signal.

* * * * *

UNITED STATES PATENT AND TRADEMARK OFFICE
CERTIFICATE OF CORRECTION

PATENT NO. : 8,262,648 B2  
APPLICATION NO. : 12/294387  
DATED : September 11, 2012  
INVENTOR(S) : Choi et al.

Page 1 of 1

It is certified that error appears in the above-identified patent and that said Letters Patent is hereby corrected as shown below:

On the Title Page Item (73) Assignee should read: Lutronic Corporation (KR)

Signed and Sealed this  
Sixth Day of May, 2014

Michelle K. Lee  
*Deputy Director of the United States Patent and Trademark Office*